United States Patent
Forbus, Jr. et al.

(10) Patent No.: US 11,820,952 B2
(45) Date of Patent: Nov. 21, 2023

(54) PROCESS TO PRODUCE LOW SHEAR STRENGTH BASE OILS

(71) Applicant: Vantage Santolubes Research LLC, New Hope, PA (US)

(72) Inventors: Thomas Reginald Forbus, Jr., Doylestown, PA (US); Salvatore Michael Perna, New Hope, PA (US)

(73) Assignee: VANTAGE SANTOLUBES RESEARCH LLC, New Hope, PA (US)

( * ) Notice: Subject to any disclaimer, the term of this patent is extended or adjusted under 35 U.S.C. 154(b) by 0 days.

(21) Appl. No.: 17/380,768

(22) Filed: Jul. 20, 2021

(65) Prior Publication Data
US 2022/0213400 A1 Jul. 7, 2022

Related U.S. Application Data (60) Provisional application No. 63/134,335, filed on Jan. 6, 2021.

(51) Int. Cl.
*C10M 105/38* (2006.01)
*C10M 105/42* (2006.01)
(Continued)

(52) U.S. Cl.
CPC ........ *C10M 105/38* (2013.01); *C10M 105/42* (2013.01); *C10M 107/32* (2013.01);
(Continued)

(58) Field of Classification Search
CPC .......... C10M 105/38; C10M 105/42; C10M 107/32; C10N 2020/04; C10N 2030/02; C10N 2030/06
See application file for complete search history.

(56) References Cited

U.S. PATENT DOCUMENTS

| 4,581,152 A | * | 4/1986 | Hotta | C07F 9/09 |
| | | | | 987/224 |
| 4,891,161 A | * | 1/1990 | Tanikawa | C10M 105/32 |
| | | | | 508/501 |

(Continued)

FOREIGN PATENT DOCUMENTS

| CN | 105431508 A | 3/2016 |
| CN | 108603137 A | 9/2018 |
| RU | 136778 U1 | 1/2014 |

OTHER PUBLICATIONS

Abdulqadir, Lawal Babatunde; "Investigation of the Effects of Soot on the Wear of Automotive Engine Components, PhD Thesis"; Department of Mechanical Engineering, The Leonardo Centre of Tribology, University of Sheffield; Nov. 2017; 230 Pages.

(Continued)

*Primary Examiner* — James C Goloboy
(74) *Attorney, Agent, or Firm* — Husch Blackwell LLP (57) ABSTRACT

A lubricating fluid comprising a base oil, which utilizes carboxylic esters of carboxyl di-end-capped-polyethylene glycols, or a mixture thereof with carboxylic esters of carboxyl di-end-capped-polytetramethylene glycols, to improve low temperature performance, as well as minimize elastohydrodynamic shear strength, and enables the production of high efficiency fluids with enhanced low temperature properties for machines or machine elements that operate in the elastohydrodynamic regime in lubrication.

23 Claims, 2 Drawing Sheets

(51) Int. Cl.
*C10M 107/32* (2006.01)
*C10N 30/02* (2006.01)
*C10N 30/06* (2006.01)
*C10N 20/04* (2006.01)

(52) U.S. Cl.
CPC ...... *C10N 2020/04* (2013.01); *C10N 2030/02* (2013.01); *C10N 2030/06* (2013.01)

(56) References Cited

U.S. PATENT DOCUMENTS

| | | | | |
|---|---|---|---|---|
| 5,173,341 | A | * | 12/1992 | Shiratori .............. C10M 149/12 152/565 |
| 5,837,401 | A | * | 11/1998 | Gauthier ............ C10M 169/041 429/231.95 |
| 9,879,198 | B2 | | 1/2018 | Forbus |
| 2009/0005275 | A1 | * | 1/2009 | Rosenbaum ......... C10M 171/02 508/110 |
| 2016/0186085 | A1 | | 6/2016 | Okamoto et al. |
| 2016/0272916 | A1 | * | 9/2016 | Kashani-Shirazi .. C08G 65/332 |
| 2017/0145336 | A1 | | 5/2017 | Forbus, Jr. |
| 2019/0322957 | A1 | | 10/2019 | Grismala |

OTHER PUBLICATIONS

International Search Report and Written Opinion of the International Searching Authority; Application No. PCT/US21/73126; Completed: Mar. 6, 2022; dated Apr. 6, 2022; 9 Pages.
Chinese Office Action; Application No. 11100547; Completed Sep. 7, 2022; 10 Pages.

\* cited by examiner

PROCESS TO PRODUCE LOW SHEAR STRENGTH BASE OILS

CROSS-REFERENCE TO RELATED APPLICATIONS

This application claims the benefit, under 35 U.S.C. § 119(e), of U.S. Provisional Application Ser. No. 63/134,335, filed on Jan. 6, 2021, the content of which is incorporated herein by reference in its entirety.

TECHNICAL FIELD

The present teachings relate generally to lubricating fluids, and more specifically to base oils for lubricants of low shear strength and good low temperature performance.

BACKGROUND

Elastohydrodynamic machine elements are mechanical devices that operate with a thin film of fluid between nominally smooth, rolling-sliding, elastically-deformed, non-conforming surfaces in mutual contact. Fluids in the elastohydrodynamic contact typically behave not as a viscous fluid, but as an elastic-plastic solid with a yield or shear strength to the normal rolling-shearing motion. Shearing within the contact only occurs when the two surfaces in contact have a differential in their relative speeds which can be caused by the geometry of the contact surfaces and their relative motion in the natural operation of machine elements.

The efficiency of these machine elements relies in large part upon the high-stress shear strength of the fluid used for lubricating the surfaces of these high-stress, elastically-deformed, non-conforming contacts. The shear strength properties of the fluid under the contact operational conditions can substantially influence their efficiency depending upon the degree of sliding motion between the mating surfaces under elastohydrodynamic conditions of lubrication. Thus, fluids with low elastohydrodynamic shear strength enable better efficiency with lower fluid shearing losses in the rolling-sliding or pure sliding motion in these contacts.

U.S. Pat. No. 9,879,198 describes low shear strength lubricating fluids composed of mixtures of carboxyl diester polytetramethylene ether glycols and closely related complex esters. Despite the low elastohydrodynamic shear strength of the lubricating fluids, they suffer from poor low temperature performance (e.g., pour point, freeze point), which limits applications where the fluids will be exposed to temperatures below −7° C. The contents of U.S. Pat. No. 9,879,198 are incorporated by reference herein in their entirety.

Thus, there exists a need for improved lubricating fluids that addresses the above problems.

SUMMARY

The needs set forth herein as well as further and other needs and advantages are addressed by the present embodiments, which illustrate solutions and advantages described below.

It is an object of the present teachings to provide base oils for lubricants to minimize their elastohydrodynamic (EHD) shear strength.

It is another object of the present teachings to provide base oils for lubricants to improve their low temperature performance.

It is another object of the present teachings to provide base oils for lubricants to enable lubrication in all applications where machine elements may operate in low temperature environments (e.g., automotive, wind turbines, alternative energy), such as temperatures equal to or less than −7° C.

It is a further object of the present teachings to provide the production of high efficiency fluids with enhanced low temperature properties for machines or machine elements that operate in the elastohydrodynamic regime in lubrication.

These and other objects of the present teachings are achieved by providing a lubricating fluid comprising: a carboxyl di-ester of polyethylene glycol having the formula:

and a carboxyl di-ester of polytetramethylene glycol having the formula:

wherein $R_1$ and $R_2$ each independently comprise linear alkyl groups each having 5 to 11 carbon atoms, and wherein m ranges from 2 to 12; and wherein $R_3$ and $R_4$ each independently comprise linear alkyl groups each having 5 to 11 carbon atoms, and wherein n ranges from 2 to 6. Each polyethylene oxide segment of the carboxyl di-ester of polyethylene glycol has an average molecular weight ranging from 200 g/mole to 400 g/mole, and each polytetramethylene oxide segment of the carboxyl di-ester of polytetramethylene glycol has an average molecular weight ranging from 200 g/mole to 300 g/mole. $R_1$ and $R_2$ are each independently derived from a mixture of octanoic carboxylic acid and decanoic carboxylic acid or derived from hexanoic carboxylic acid. $R_3$ and $R_4$ are each independently derived from a mixture of octanoic carboxylic acid and decanoic carboxylic acid or derived from hexanoic carboxylic acid.

The lubricating fluid has a traction coefficient ranging from 0.026 μ to 0.008 μ when measured at a slide-to-roll ratio of 190 percent at 1.0 GPa maximum contact stress at 40° C. to 120° C. for 1 to 3 m/s entrainment velocity. The lubricating fluid has a 40° C. Kinematic Viscosity ranging from 13 cSt to 21 cSt. The lubricating fluid has a Viscosity Index ranging from 183 to 213. The lubricating fluid has a Freeze Point below −7° C.

The lubricating fluid of further comprises at least one additive selected from the group consisting of: oxidation inhibitors, metallic dispersants, non-metallic dispersants, metallic detergents, non-metallic detergents, corrosion inhibitors, rust inhibitors, metal deactivators, metallic anti-wear agents, non-metallic anti-wear agents, phosphorus- containing anti-wear agents, non-phosphorus containing anti-wear agents, sulfur-containing anti-wear agents, non-sulfur containing anti-wear agents, metallic extreme pressure additives, non-metallic extreme pressure additives, phosphorus-containing extreme pressure additives, non-phosphorus containing extreme pressure additives, sulfur-containing extreme pressure additives, non-sulfur containing extreme pressure additives, anti-seizure agents, pour point depressants, wax modifiers, viscosity modifiers, seal compatibility agents, friction modifiers, lubricity agents, anti-staining agents, chromophoric agents, defoamants, demulsifiers, and a combination thereof. The lubricating fluid further comprises at least one lubricant base oil selected from a group consisting of: mineral oil, polyalphaolefin, ester, polyalkylene glycol, ethylene-propylene oil, silicone oil, and a combination thereof.

The present teachings also provide a lubricating fluid comprising a carboxyl di-ester composition independently selected from the group consisting of: a carboxyl di-ester of polyethylene glycol having the formula:

(1)

wherein $R_1$ and $R_2$ each independently comprise linear alkyl groups each having 5 to 11 carbon atoms, and wherein m ranges from 2 to 12; a complex carboxyl di-ester of polyethylene glycol having the formula:

(3)

wherein $R_6$ and $R_7$ each independently comprise linear alkyl groups each having 5 to 11 carbon atoms, wherein $R_5$ comprises linear alkyl group having 24 to 36 carbon atoms, wherein o ranges from 2 to 12, and wherein p ranges from 2 to 12; a complex carboxyl di-ester of polyethylene glycol and polytetramethylene glycol having the formula:

(4)

wherein $R_9$ and $R_{10}$ each independently comprise linear alkyl groups each having 5 to 11 carbon atoms, wherein $R_8$ comprises linear alkyl group having 24 to 36 carbon atoms, wherein q ranges from 2 to 12, and wherein r ranges from 2 to 6; and a mixture thereof. Each polyethylene oxide segment of formulas (1), (3), and (4) has an average molecular weight ranging from 200 to 400 g/mole and each polytetramethylene oxide segment of formula (4) has an average molecular weight ranging from 200 to 300 g/mole. $R_1$ and $R_2$ are each independently derived from a mixture of octanoic carboxylic acid and decanoic carboxylic acid or derived from hexanoic carboxylic acid. $R_6$ and $R_7$ are each independently derived from a mixture of octanoic carboxylic acid and decanoic carboxylic acid or derived from hexanoic carboxylic acid. $R_9$ and $R_{10}$ are each independently derived from a mixture of octanoic carboxylic acid and decanoic carboxylic acid or derived from hexanoic carboxylic acid. $R_5$ and $R_8$ are each derived from a dicarboxylic acid having 24 to 36 carbon atoms.

The lubricating fluid has a traction coefficient ranging from 0.026 μ to 0.008 μ when measured at a slide-to-roll ratio of 190 percent at 1.0 GPa maximum contact stress at 40° C. to 120° C. for 1 to 3 m/s entrainment velocity. The lubricating fluid has a Freeze Point below −7° C.

The lubricating fluid further comprises at least one additive selected from the group consisting of: oxidation inhibitors, metallic dispersants, non-metallic dispersants, metallic detergents, non-metallic detergents, corrosion inhibitors, rust inhibitors, metal deactivators, metallic anti-wear agents, non-metallic anti-wear agents, phosphorus-containing anti-wear agents, non-phosphorus containing anti-wear agents, sulfur-containing anti-wear agents, non-sulfur containing anti-wear agents, metallic extreme pressure additives, non-metallic extreme pressure additives, phosphorus-containing extreme pressure additives, non-phosphorus containing extreme pressure additives, sulfur-containing extreme pressure additives, non-sulfur containing extreme pressure additives, anti-seizure agents, pour point depressants, wax modifiers, viscosity modifiers, seal compatibility agents, friction modifiers, lubricity agents, anti-staining agents, chromophoric agents, defoamants, demulsifiers, and a combination thereof. The lubricating fluid further comprises at least one lubricant base oil selected from a group consisting of: mineral oil, polyalphaolefin, ester, polyalkylene glycol, ethylene-propylene oil, silicone oil, and a combination thereof.

Other features and aspects of the present teachings will become apparent from the following detailed description, taken in conjunction with the accompanying drawings, which illustrate by way of example the features in accordance with embodiments of the present teachings. The summary is not intended to limit the scope of the present teachings, which is defined by the claims included herein.

DETAILED DESCRIPTION

The present teachings are described more fully hereinafter with reference to the accompanying drawings, in which the present embodiments are shown. The following description illustrates the present teachings by way of example, not by way of limitation of the principles of the present teachings.

The present teachings have been described in language more or less specific as to structural features. It is to be understood, however, that the present teachings are not limited to the specific features shown and described, since the product and/or method herein disclosed comprises preferred forms of putting the present teachings into effect.

Generally, all terms used in the claims are to be interpreted according to their ordinary meaning in the technical field, unless explicitly defined otherwise herein. All references to a/an/the element, apparatus, component, means, step, etc. are to be interpreted openly as referring to at least one instance of the element, apparatus, component, means, step, etc., unless explicitly stated otherwise. Other than in the operating examples, or where otherwise indicated, all numbers expressing quantities of ingredients or reaction conditions used herein are to be understood as modified in all instances by the term "about".

The present teachings provide base oils for formulated lubricants of low elastohydrodynamic shear strength and good low temperature performance for the production of lubricating fluids of high energy efficiency and improved low temperature properties for elastohydrodynamic lubrication.

Base Oils

The present teachings utilize carboxylic esters of carboxyl di-end-capped-polyethylene glycols, or a mixture thereof with carboxylic esters of carboxyl di-end-capped-polytetramethylene glycols, to improve low temperature performance of lubricating fluids, as well as minimize their elastohydrodynamic (EHD) shear strength, and enable the production of high efficiency fluids with enhanced low temperature properties for machines or machine elements that operate in the elastohydrodynamic regime of lubrication.

The present teachings provide a lubricating base oil comprising a carboxyl di-ester of polyethylene glycol. In one embodiment, the carboxyl di-ester of polyethylene glycol has the structure of formula (1):

(1)

$R_1$ and $R_2$ may each independently comprise linear alkyl groups each having 5 to 11 carbon atoms. In other examples, $R_1$ and $R_2$ may each independently comprise linear alkyl groups each having 7 to 9 carbon atoms. Further, in other examples, $R_1$ and $R_2$ each may contain branched alkyl groups having 5 to 11 carbon atoms or 7 to 9 carbon atoms, wherein the amount of branched alkyl groups in combination of $R_1$ and $R_2$ is less than 10 wt. %, less than 5 wt. %, or less than 1 wt. % of the total weight of carboxyl di-ester of polyethylene glycol.

In some examples, $R_1$ and $R_2$ each may be independently derived from a mixture of octanoic carboxylic acid and decanoic carboxylic acid. Still, in other examples, $R_1$ and $R_2$ are each independently derived from hexanoic carboxylic acid.

In some embodiments of formula (1), m ranges from 2 to 12, preferably from 3 to 11.

Each polyethylene oxide segment of the carboxyl di-ester of polyethylene glycol of formula (1) has an average molecular weight ranging from 200 g/mole to 400 g/mole. The carboxyl di-ester of polyethylene glycol of formula (1) may be a liquid at 25° C.

The lubricating fluid comprising the carboxyl di-ester of polyethylene glycol of formula (1) has low viscosity.

The lubricating fluids containing the carboxyl di-ester of polyethylene glycol of formula (1) possess extremely low shear strength in elastohydrodynamic sliding and rolling-sliding contacts and will therefore enable fluids used in elastohydrodynamic lubrication to be produced that have high energy efficiency from low shearing losses. In one embodiment, the lubricating fluid comprising the carboxyl di-ester of polyethylene glycol of formula (1) has a traction coefficient ranging from 0.026 µ to 0.008 µ when measured at a slide-to-roll ratio of 190 percent at 1.0 GPa maximum contact stress at 40° C. to 120° C. for 1 to 3 m/s entrainment velocity.

The lubricating fluids containing the carboxyl di-ester of polyethylene glycol of formula (1) also possess extremely low freeze point that improves the low temperature performance of the lubricating fluids, which can be used in all applications where machine elements may operate in low temperature environments (e.g., automotive, wind turbines, alternative energy). In one embodiment, the lubricating fluid comprising the carboxyl di-ester of polyethylene glycol of formula (1) has a freeze point ranging from −25° C. to −38° C.

The present teachings also provide a lubricating base oil comprising a mixture of a carboxyl di-ester of polyethylene glycol as described above and a carboxyl di-ester of polytetramethylene glycol as described below. In one embodiment, the carboxyl di-ester of polytetramethylene glycol has the structure of formula (2).

(2)

$R_3$ and Ra may each independently comprise linear alkyl groups each having 5 to 11 carbon atoms. In other examples, $R_3$ and Ra may each independently comprise linear alkyl groups each having 7 to 9 carbon atoms. Further, in other examples, $R_3$ and Ra each may contain branched alkyl groups having 5 to 11 carbon atoms or 7 to 9 carbon atoms, wherein the amount of branched alkyl groups in combination of $R_3$ and $R_4$ is less than 10 wt. %, less than 5 wt. %, or less than 1 wt. % of the total weight of carboxyl di-ester of polytetramethylene glycol.

In some examples, $R_3$ and Ra each may be independently derived from a mixture of octanoic carboxylic acid and decanoic carboxylic acid. Still, in other examples, $R_3$ and $R_4$ are each independently derived from hexanoic carboxylic acid.

In some embodiments of formula (2), n ranges from 2 to 6, preferably from 2 to 4.

Each polytetramethylene oxide segment of the carboxyl di-ester of polytetramethylene glycol in formula (2) has an average molecular weight ranging from 200 g/mole to 300 g/mole. The carboxyl di-ester of polytetramethylene glycol of formula (2) may be a liquid at 25° C.

The carboxyl di-ester of polyethylene glycol and the carboxyl di-ester of polytetramethylene glycol are blended at ratios to obtain a product having a desired ISO viscosity grade. In some embodiments, the lubricating fluid comprising a mixture of the carboxyl di-ester of polyethylene glycol of formula (1) and the carboxyl di-ester of polytetramethylene glycol of formula (2) has low viscosity.

The lubricating fluids containing a mixture of the carboxyl di-ester of polyethylene glycol of formula (1) and the carboxyl di-ester of polytetramethylene glycol of formula (2) possess extremely low shear strength in elastohydrodynamic sliding and rolling-sliding contacts and will therefore enable fluids used in elastohydrodynamic lubrication to be produced that have high energy efficiency from low shearing losses. In one embodiment, the lubricant fluid comprising a mixture of formula (1) and formula (2) has a traction coefficient ranging from 0.026 µ to 0.008 µ when measured at a slide-to-roll ratio of 190 percent at 1.0 GPa maximum contact stress at 40° C. to 120° C. for 1 to 3 m/s entrainment velocity.

The lubricating fluids containing a mixture of the carboxyl di-ester of polyethylene glycol of formula (1) and the carboxyl di-ester of polytetramethylene glycol of formula (2) also possess extremely low freeze point that improves the low temperature performance of the lubricating fluids, which can be used in all applications where machine elements may operate in low temperature environments (e.g., automotive, wind turbines, alternative energy). In one embodiment, the lubricating fluid comprising a mixture of formula (1) and formula (2) has a freeze point ranging from −11° C. to −34° C.

The present teachings also provide a lubricating base oil comprising a complex carboxyl di-ester of polyethylene glycol. In one embodiment, the complex di-ester of polyethylene glycol has the structure of formula (3).

(3)

$R_6$ and $R_7$ may each independently comprise linear alkyl groups each having 5 to 11 carbon atoms. In other examples, $R_6$ and $R_7$ may each independently comprise linear alkyl groups each having 7 to 9 carbon atoms. Further, in other examples, $R_6$ and $R_7$ each may contain branched alkyl groups having 5 to 11 carbon atoms or 7 to 9 carbon atoms, wherein the amount of branched alkyl groups in combination of $R_6$ and $R_7$ is less than 10 wt. %, less than 5 wt. %, or less than 1 wt. % of the total weight of carboxyl di-ester of polyethylene glycol.

In some examples, $R_6$ and $R_7$ each may be independently derived from a mixture of octanoic carboxylic acid and decanoic carboxylic acid. Still, in other examples, $R_6$ and $R_7$ are each independently derived from hexanoic carboxylic acid.

$R_5$ may comprise linear alkyl groups having 24-36 carbon atoms and may be derived from a dicarboxylic acid. In some examples, $R_5$ may comprise linear alkyl groups having 26-34 carbon atoms and may be derived from a dicarboxylic acid. In some examples, $R_5$ may comprise linear alkyl groups having 28-32 carbon atoms and may be derived from a dicarboxylic acid.

In some embodiments of formula (3), o ranges from 2 to 12, preferably from 3 to 11. In some embodiments of formula (3), p ranges from 2 to 12, preferably from 3 to 11.

Each polyethylene oxide segment of the carboxyl di-ester of polyethylene glycol of formula (3) has an average molecular weight ranging from 200 g/mole to 400 g/mole. The carboxyl di-ester of polyethylene glycol of formula (3) may be a liquid at 25° C.

The lubricating fluid comprising the carboxyl di-ester of polyethylene glycol of formula (3) has high viscosity.

The lubricating fluids containing the carboxyl di-ester of polyethylene glycol of formula (3) possess extremely low shear strength in elastohydrodynamic sliding and rolling-sliding contacts and will therefore enable fluids used in elastohydrodynamic lubrication to be produced that have high energy efficiency from low shearing losses.

The lubricating fluids containing the carboxyl di-ester of polyethylene glycol of formula (3) also possess extremely low freeze point that improves the low temperature performance of the lubricating fluids, which can be used in all applications where machine elements may operate in low temperature environments (e.g., automotive, wind turbines, alternative energy). In one embodiment, the lubricating fluid comprising the carboxyl di-ester of polyethylene glycol of formula (3) has a freeze point ranging from −31° C. to −40° C.

The present teachings also provide a lubricating base oil comprising a complex carboxyl di-ester of polyethylene glycol and polytetramethylene glycol. In one embodiment, the complex carboxyl di-ester of polyethylene glycol and polytetramethylene glycol has the structure of formula (4).

(4)

$R_9$ and $R_{10}$ may each independently comprise linear alkyl groups each having 5 to 11 carbon atoms. In other examples, $R_9$ and $R_{10}$ may each independently comprise linear alkyl groups each having 7 to 9 carbon atoms. Further, in other examples, $R_9$ and $R_{10}$ each may contain branched alkyl groups having 5 to 11 carbon atoms or $R_9$ and $R_{10}$ carbon atoms, wherein the amount of branched alkyl groups in combination of $R_9$ and $R_{10}$ is less than 10 wt. %, less than 5 wt. %, or less than 1 wt. % of the total weight of carboxyl di-ester of polyethylene glycol.

In some examples, $R_9$ and $R_{10}$ each may be independently derived from a mixture of octanoic carboxylic acid and decanoic carboxylic acid. Still, in other examples, $R_9$ and $R_{10}$ are each independently derived from hexanoic carboxylic acid.

$R_8$ may comprise linear alkyl groups having 24-36 carbon atoms and may be derived from a dicarboxylic acid. In some examples, $R_8$ may comprise linear alkyl groups having 26-34 carbon atoms and may be derived from a dicarboxylic acid. In some examples, $R_8$ may comprise linear alkyl groups having 28-32 carbon atoms and may be derived from a dicarboxylic acid.

In some embodiments of formula (4), q ranges from 2 to 12, preferably from 3 to 11. In some embodiments of formula (3), r ranges from 2 to 6, preferably from 2 to 4.

Each polyethylene oxide segment of the carboxyl di-ester of polyethylene glycol and polytetramethylene glycol of formula (4) has an average molecular weight ranging from 200 g/mole to 400 g/mole, and each polyethylene oxide segment of the carboxyl di-ester of polyethylene glycol and polytetramethylene glycol of formula (4) has an average molecular weight ranging from 200 g/mole to 400 g/mole. The carboxyl di-ester of polyethylene glycol and polytetramethylene glycol of formula (4) may be a liquid at 25° C.

The lubricating fluid comprising the carboxyl di-ester of polyethylene glycol and polytetramethylene glycol of formula (4) has high viscosity.

The lubricating fluids containing the carboxyl di-ester of polyethylene glycol and polytetramethylene glycol of formula (4) possess extremely low shear strength in elastohydrodynamic sliding and rolling-sliding contacts and will therefore enable fluids used in elastohydrodynamic lubrication to be produced that have high energy efficiency from low shearing losses.

The lubricating fluids containing the carboxyl di-ester of polyethylene glycol and polytetramethylene glycol of formula (4) also possess extremely low freeze point that improves the low temperature performance of the lubricating fluids, which can be used in all applications where machine elements may operate in low temperature environments (e.g., automotive, wind turbines, alternative energy). In one embodiment, the lubricating fluid comprising the carboxyl di-ester of polyethylene glycol and polytetramethylene glycol of formula (4) has a freeze point ranging from −31° C. to −40° C.

Synthetic Processes of Base Oils

The following examples further describe and demonstrate illustrative embodiments within the scope of the present teachings. The examples are given solely for illustration and are not to be construed as limitations of this invention as many variations are possible without departing from the spirit and scope thereof. For example, the mixture of normal C8 and 010 carboxylic acids may have a weight ratio different from the examples of 60/40 or 80/20 used below, and may have a weight ratio between 60/40 and 80/20.

Example 1: Preparation of Carboxyl Di-Ester of Polyethylene Glycol of Formula (1) (e.g., Peg 300 with Nc6 Acid)

A 1000 mL five-neck round-bottom flask equipped with an overhead mechanical stirrer, a gas dispersion tube, and a Dean-Stark trap fitted with a cold-water condenser were used as the synthesis reactor. To the vessel was added 299.2 grams (1 mol) of polyethylene glycol 300 (polyethylene glycol of nominal average molecular weight of 300 Daltons), 255.5 grams (2.20 mol) of hexanoic acid (e.g., normal C6 carboxylic acid), 10 grams of xylenes, 0.7 grams of sodium hypophosphite, and 0.05 grams of dibutyltin oxide. Here, xylene is the azeotropic agent, sodium hypophosphite is the antioxidant, and dibutyltin oxide is the catalyst. Nitrogen blanketed the reaction with a roughly 30 mL/min flow and used throughout the reaction and stripping. The temperature of the flask contents was raised to 165° C. and maintained at 165° C. until the theoretical amount of water is collected in the Dean-Stark trap.

The hydroxyl content of the mixture is checked, and the reaction is considered complete when the hydroxyl number is less than 1 mg KOH/g. Excess xylenes and hexanoic acid are then removed from the crude product under reduced pressure (5 mm Hg). The crude product is then treated with calcium carbonate (or sodium carbonate, any suitable alkali metal carbonate, propylene carbonate, or glycidyl neodecanoate) to reduce the acid number (i.e., carboxylic acid content) to 0.1 mg KOH/g or less. The resulting slurry is then filtered yielding 479 g (97% yield) of product. The resulting product has a kinematic viscosity at 100° C. of 3.8 cSt, a VI (viscosity index) of 183, and a freezing point of −38° C.

It is noted that although the hexanoic acid (e.g., normal C6 carboxylic acid) is used here, the octanoic/decanoic acid (e.g., a mixture of normal C8 and 010 carboxylic acids at a weight ratio of 60/40 or 80/20) may be used as replacement or supplement.

Example 2: Preparation of a Mixture of a Carboxyl Di-Ester of Polytetramethylene Glycol of Formula (2) (e.g., Ptmeg 250 with Nc8-10 (60/40 or 80/20 Nc8-10 Weight Ratio) Acids) and a Carboxyl Di-Ester of Polyethylene Glycol of Formula (1) (e.g., Peg 300 with Nc8-10 (60/40 or 80/20 Nc8-10 Weight Ratio) Acids)

A 1000 mL five-neck round-bottom flask equipped with an overhead mechanical stirrer, a gas dispersion tube, and a Dean-Stark trap fitted with a cold-water condenser was used as the synthesis reactor. To the vessel was added 145.4 grams (0.57 mol) of polytetramethylene glycol 250 (polytetramethylene glycol of nominal average molecular weight of 250 Daltons), 145.4 grams (0.49 mol) of polyethylene glycol 300 (polyethylene glycol of nominal average molecular weight of 300 Daltons), 340 grams (2.20 mol) of octanoic/decanoic acid (e.g., a mixture of normal C8 and 010 carboxylic acids at a weight ratio of 60/40 or 80/20), 10 grams of xylenes, 0.7 grams of sodium hypophosphite, and 0.02 grams of dibutyltin oxide. Here, xylene is the azeotropic agent, sodium hypophosphite is the antioxidant, and dibutyltin oxide is the catalyst. Nitrogen blanketed the reaction with a roughly 30 mL/min flow and used throughout the reaction and stripping. The temperature of the flask contents was raised to 165° C. and maintained at 165° C. until the theoretical amount of water is collected in the Dean-Stark trap.

The hydroxyl content of the mixture is checked, and the reaction is considered complete when the hydroxyl number is less than 1 mg KOH/g. Excess xylenes, octanoic acid, and decanoic acid are then removed from the crude product under reduced pressure (5 mm Hg). The crude product is then treated with calcium carbonate (or sodium carbonate, any suitable alkali metal carbonate, propylene carbonate, or glycidyl neodecanoate) to reduce the acid number (i.e., carboxylic acid content) to 0.1 mg KOH/g or less. The resulting slurry is then filtered yielding 562 g (97% yield of theoretical yield of 579.4 grams) of product. The resulting product has a kinematic viscosity at 100° C. of 4.6 cSt, a VI (viscosity index) of 200, and a freezing point of −15° C.

It is noted that although the octanoic/decanoic acid (e.g., a mixture of normal C8 and 010 carboxylic acids at a weight ratio of 60/40 or 80/20) is used here, the hexanoic acid (e.g., normal C6 carboxylic acid) may be used as replacement or supplement.

Example 3: Preparation of a Complex Carboxyl Di-Ester of Polyethylene Glycol of Formula (3) (e.g., Peg 300 with Oleic Dimer Acid and Nc8-10 (60/40 or 80/20 Nc8-10 Weight Ratio) Acids)

A 1000 mL five-neck round-bottom flask equipped with an overhead mechanical stirrer, a gas dispersion tube, and a Dean-Stark trap fitted with a cold-water condenser was used as the synthesis reactor. To the vessel was added 294.9 grams (1 mol) of polyethylene glycol 300 (polyethylene glycol of nominal average molecular weight of 300 Daltons), 281.8 grams (0.5 mol) of oleic dimer acid, 10 grams of xylenes, and 0.7 grams of sodium hypophosphite. Here, xylene is the azeotropic agent, and sodium hypophosphite is the antioxidant. Nitrogen blanketed the reaction with a roughly 30 mL/min flow and used throughout the reaction and stripping. The temperature of the flask contents was raised to 185° C. and maintained at 185° C. The acid number of the mixture is checked, and when the acid number is 18 mg KOH/g, 0.05 grams of dibutyltin oxide as catalyst is added to the flask and the temperature is increased to 195° C. The temperature is maintained at 195° C. until the acid number is checked as 0.4 mg KOH/g. The temperature is then reduced to 100° C. and 167.7 grams (1.1 mol) of octanoic/decanoic acid (e.g., a mixture of normal C8 and C10 carboxylic acids at a weight ratio of 60/40 or 80/20) is added to the flask with 10 grams of additional xylenes. The temperature is then increased to 195° C. and maintained until the theoretical amount of water is collected in the dean-stark trap.

The hydroxyl number of the mixture is checked, and the reaction is considered complete when the hydroxyl number is 10 mg KOH/g or less. Excess xylenes, octanoic acid, and decanoic acid are then removed from the crude product under reduced pressure (5 mm Hg) at the temperature ranging from 195° C. to 205° C. The crude product is then treated with propylene carbonate (or calcium carbonate, sodium carbonate, any suitable alkali metal carbonate, or glycidyl neodecanoate) at the temperature 215° C. to reduce the acid number (i.e., carboxylic acid content) to 0.1 mg KOH/g or less. The resulting slurry is then filtered. The resulting product has a kinematic viscosity at 100° C. of 65 cSt, a VI (viscosity index) of 191, and a freezing point of −31° C. The resulting product is liquid at 25° C.

It is noted that although the octanoic/decanoic acid (e.g., a mixture of normal C8 and C10 carboxylic acids at a weight ratio of 60/40 or 80/20) is used here, the hexanoic acid (e.g., normal C6 carboxylic acid) may be used as replacement or supplement.

Example 4: Preparation of a Complex Carboxyl Di-Ester of Polyethylene Glycol and Polytetramethylene Glycol of Formula (4) (e.g., Ptmeg 250 & Peg 300 with Oleic Dimer Acid and Nc8-10 (60/40 or 80/20 Nc8-10 Weight Ratio) Acids)

A 1000 mL five-neck round-bottom flask equipped with an overhead mechanical stirrer, a gas dispersion tube, and a Dean-Stark trap fitted with a cold-water condenser was used as the synthesis reactor. To the vessel was added 148.9 grams (0.5 mol) of polyethylene glycol 300 (polyethylene glycol of nominal average molecular weight of 300 Daltons), 148.9 grams (0.6 mol) of polytetramethylene glycol 250 (polytetramethylene glycol of nominal average molecular weight of 250 Daltons), 280.4 grams (0.5 mol) of oleic dimer acid, 10 grams of xylenes, and 0.7 grams of sodium hypophosphite. Here, xylene is the azeotropic agent, and sodium hypophosphite is the antioxidant. Nitrogen blanketed the reaction with a roughly 30 mL/min flow and used throughout the reaction and stripping. The temperature of the flask contents was raised to 195° C. and maintained at 195° C. The acid number of the mixture is checked, and when the acid number is 18 mg KOH/g, 0.05 grams of dibutyltin oxide as catalyst is added to the flask. The temperature is maintained at 195° C. until the acid number is checked as 0.4 mg KOH/g. The temperature is then reduced to 100° C. and 166.5 grams (1.1 mol) of octanoic/decanoic acid (e.g., a mixture of normal C8 and C10 carboxylic acids at a weight ratio of 60/40 or 80/20) is added to the flask with 10 grams of additional xylenes. The temperature is then increased to 195° C. and maintained until the theoretical amount of water is collected in the dean-stark trap.

The hydroxyl number of the mixture is checked, and the reaction is considered complete when the hydroxyl number is 10 mg KOH/g or less. Excess xylenes, octanoic acid, and decanoic acid are then removed from the crude product under reduced pressure (5 mm Hg) at the temperature ranging from 195° C. to 205° C. The crude product is then treated with propylene carbonate (or calcium carbonate, sodium carbonate, any suitable alkali metal carbonate, or glycidyl neodecanoate) at the temperature 215° C. to reduce the acid number (i.e., carboxylic acid content) to 0.1 mg KOH/g or less. The resulting slurry is then filtered. The resulting product has a kinematic viscosity at 100° C. of 75.2 cSt, a VI (viscosity index) of 196, and a freezing point of −35° C. The resulting product is liquid at 25° C.

It is noted that although the octanoic/decanoic acid (e.g., a mixture of normal C8 and C10 carboxylic acids at a weight ratio of 60/40 or 80/20) is used here, the hexanoic acid (e.g., normal C6 carboxylic acid) may be used as replacement or supplement.

Characterizations of Base Oils with or without Additives

The lubricating fluids of the present teachings may be characterized by a variety of standard tests known to one of ordinary skill in the art. The energy efficiency of the lubricating fluids may be affected by the viscosity of the lubricating fluids and the traction coefficient of the lubricating fluids. The viscosity of the lubricating fluids is closely related to its ability to reduce friction in the contracts between solid surfaces. The traction coefficient of the lubricating fluids is related to the energy losses with a certain load.

man Traction coefficients may be measured using PCS Mini-Traction Machine (MTM) from PCS Instruments, Ltd. measured at various slide-to-roll ratios (e.g., 0.1% to 200%), temperatures, and loads ranging from 20N to 70N or a maximum Hertzian contact stress of 0.5 GPa to 1.5 GPa.

Figure 1:
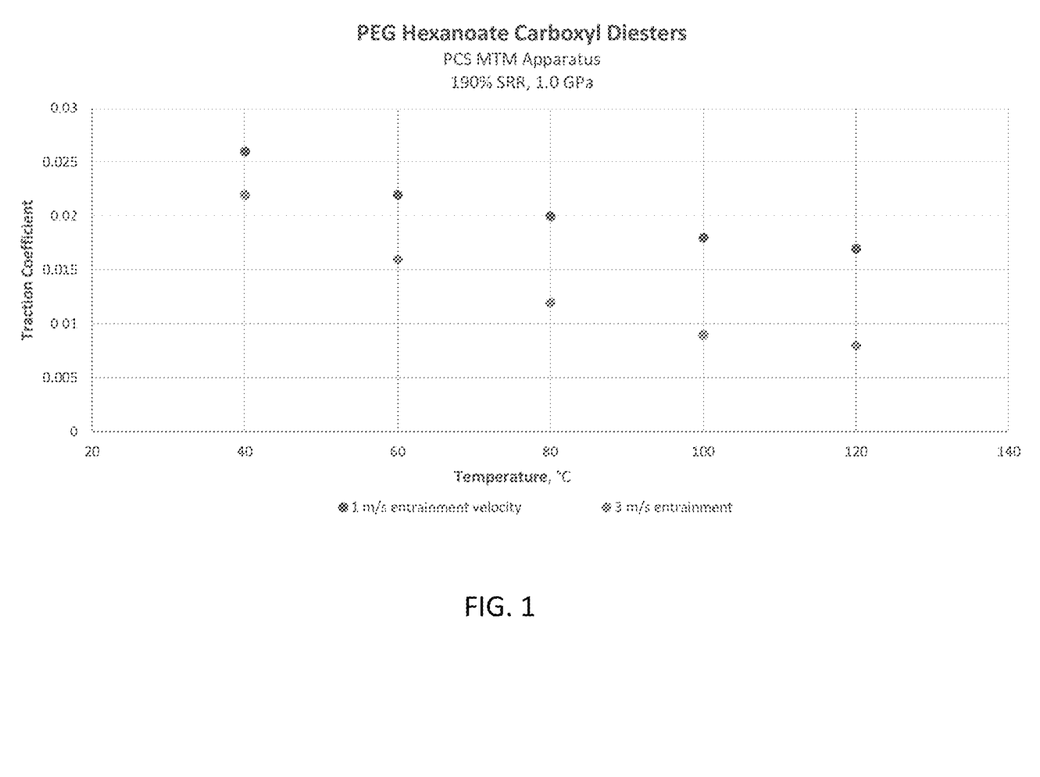
FIG. 1 illustrates the plots of temperature versus traction coefficient, ρ, measured at maximum contact stress of 1.0 GPa, 190% slide/roll ratio, and an entrainment speed to 1 and 3 meters/second for one embodiment of the lubricating fluid according to the present teachings.

Referring to FIG. 1, the traction coefficients is measured at 190% various slide-to-roll ratio, different temperatures 40° C., 60° C., 80° C., 100° C., and 120° C., a maximum Hertzian contact stress of 1.0 GPa, and an entrainment speed of 1 and 3 meters/second. The lubricating fluid tested in FIG. 1 is the carboxyl di-esters of polyethylene glycol of formula (1) having PEG 300 with nC6 Acid. As shown in FIG. 1, the lubricant fluid has traction coefficients of 0.026, 0.022, 0.020, 0.018 and 0.017 Limiting Shear Stress (at 190% sliding) when measured on a steel-on-steel point contact (PCS MTM apparatus) at 1.0 GPa maximum contact stress and 1 meter/sec entrainment velocity at 40, 60, 80, 100 and 120° C., respectively, and 0.022, 0.016, 0.012, 0.009 and 0.008 at 3.0 meters/sec entrainment velocity.

Viscosity, often referred to as Dynamic Viscosity (DV), can be measured using Kinematic Viscosity (KV). Kinematic Viscosity (KV) may be determined by ASTM D445-06 Standard Test Method for Kinematic Viscosity of Transparent and Opaque Liquids (and Calculation of Dynamic Viscosity). Kinematic Viscosity may also be calculated from a measurement of Dynamic Viscosity (DV) at low shear rates and density using the equation:

$$KV = \frac{DV}{\rho}$$

where ρ is density.

Viscosity Index (VI) is a unitless measurement of a lubricating fluid's change in viscosity relative to temperature change. The higher the VI, the more stable the viscosity remains over temperature fluctuations. Viscosity Index may be determined by ASTM D2270-04 Standard Practice for Calculating Viscosity Index From Kinematic Viscosity at 40° C. and 100° C.

The following Tables 1-4 illustrate some examples of the lubricating fluids of the present teachings compared with existing art in the measurement of DV, KV, VI, and freeze point.

TABLE 1

Carboxyl di-ester of PTMEG 250 and carboxyl di-ester of
EG 300 Diols with nC8-10 (60/40 nC8-10 weight ratio) Acids

|  | Comparative Example | Inventive Examples | | | |
| --- | --- | --- | --- | --- | --- |
| PTMEG 250 (wt. %) | 100 | 75 | 50 | 25 | 0 |
| PEG 300 (wt. %) | 0 | 25 | 50 | 75 | 100 |
| DV at 0° C. (cP) | 109.8 | 93.2 | 91.6 | 98.1 | 103.5 |
| DV at −10° C. (cP) | N/A | 170.8 | 172.2 | 190.2 | 208.7 |
| DV at −20° C. (cP) | N/A | N/A | N/A | N/A | 400.7 |
| KV at 40° C. (cSt) | 21.0 | 17.9 | 17.3 | 17.2 | 17.8 |
| KV at 100° C. (cSt) | 5.4 | 4.7 | 4.6 | 4.6 | 4.6 |
| VI | 213 | 204 | 200 | 202 | 190 |
| Freeze Point (° C.) | −7 | −11 | −15 | −18 | −25 |

TABLE 2

Carboxyl di-ester of PTMEG 250 and carboxyl di-ester of
PEG 300 Diols with nC8-10 (80/20 nC8-10 weight ratio) Acids

|  | Comparative Example | Inventive Examples | | | |
| --- | --- | --- | --- | --- | --- |
| PTMEG 250 (wt. %) | 100 | 75 | 50 | 25 | 0 |
| PEG 300 (wt. %) | 0 | 25 | 50 | 75 | 100 |
| DV at 0° C. (cP) | 97.8 | 86.8 | 75.4 | 90.9 | 98.1 |
| DV at −10° C. (cP) | 175.7 | 158.3 | 114.2 | 163.4 | 175.2 |
| DV at −20° C. (cP) | N/A | N/A | N/A | N/A | 336.2 |
| KV at 40° C. (cSt) | 18.4 | 15.6 | 15.5 | 15.6 | 16 |
| KV at 100° C. (cSt) | 4.9 | 4.3 | 4.3 | 4.3 | 4.4 |
| VI | 208 | 202 | 204 | 204 | 205 |
| Freeze Point (° C.) | −11 | −15 | −18 | −20 | −28 |

TABLE 3

Carboxyl di-ester of PTMEG 250 and carboxyl di-ester
of PEG 300 Diols with nC6 Acids

|  | Comparative Example | Inventive Examples | | | |
| --- | --- | --- | --- | --- | --- |
| PTMEG 250 (wt. %) | 100 | 75 | 50 | 25 | 0 |
| PEG 300 (wt. %) | 0 | 25 | 50 | 75 | 100 |
| DV at 0° C. (cP) | 62.8 | 70.7 | 64.0 | 72.2 | 80.9 |
| DV at −10° C. (cP) | 109.2 | 127.6 | 115.9 | 139.8 | 154.0 |
| DV at −20° C. (cP) | N/A | 329.2 | 234.9 | 288.7 | 335.9 |
| DV at −30° C. (cP) | N/A | N/A | 468.1 | 553.4 | 638.1 |
| KV at 40° C. (cSt) | 13.42 | 14.98 | 14.36 | 13.7 | 13.65 |
| KV at 100° C. (cSt) | 3.85 | 4.24 | 4.07 | 3.86 | 3.79 |
| VI | 200 | 210 | 203 | 192 | 183 |
| Freeze Point (° C.) | −18 | −24 | −−31 | −34 | −38 |

TABLE 4

Complex Carboxyl Di-ester Compositions

| Complex Carboxyl Di-ester Composition | DV at 0° C. (cP) | DV at −10° C. (cP) | DV at −20° C. (cP) | DV at −30° C. (cP) | KV at 40° C. (cSt) | KV at 100° C. (cSt) | VI | Freeze Point (° C.) |
|---|---|---|---|---|---|---|---|---|
| PTMEG 250 with Oleic Dimer Acid and nC8/10 (60/40) Acid | 7349.6 | 17070 | N/A | N/A | 658.3 | 81.4 | 205 | −13 |
| PTMEG 250 with Oleic Dimer Acid and nC6 Acid | 4204.6 | 8533.2 | 17254 | N/A | 593.6 | 74.1 | 206 | −24 |
| PEG 300 with Oleic Dimer Acid and nC8/10 (60/40) Acid | 6907.9 | 13429 | 27219 | 52344 | 559.1 | 65.0 | 191 | −31 |
| PEG 300 with Oleic Dimer Acid and nC8/10 (80/20) Acid | 6473.3 | 12662 | 24351 | N/A | 576.2 | 67.2 | 193 | −29 |
| PEG 300 with Oleic Dimer Acid and nC6 Acid | 5417.9 | 10376 | 19071 | 36681 | 556.8 | 64.7 | 191 | −40* |
| PTMEG 250 and PEG 300 with Oleic Dimer Acid and nC8/10 (60/40) Acid | 4852.1 | 10189 | 18341 | 36682 | 654.8 | 75.2 | 196 | −35 |

Additives

The various embodiments of lubricating fluids according to the present teachings may further comprise at least one additive that in some embodiments may be selected from the group consisting of: dispersant, detergent, defoamer, antioxidant, rust inhibitor, friction modifier, corrosion inhibitor, extreme pressure additive, anti-wear additive, pour point depressant, and combinations thereof.

Examples of the dispersant, including ashless dispersant, according to the present teachings may include one or more of those based on polybutenyl succinic acid imide, polybutenyl succinic acid amide, benzylamine, succinic acid ester, succinic acid ester-amide, or a boron derivative thereof. The ashless dispersant may be incorporated normally at 0.05 wt. % to 7 wt. % of the total weight of the lubricating fluid.

Examples of the detergent, including metallic detergent, according to the present teachings may include one or more of those containing a sulfonate, phenate, salicylate, and phosphate of calcium, phosphate of magnesium, phosphate of barium, or the like. It may be optionally selected from perbasic, basic, neutral salts, and so forth of different acid value. The metallic detergent is optionally incorporated at 0.05 wt. % to 5 wt. % of the total weight of the lubricating fluid.

Examples of the defoamer according to the present teachings may include one or more of polydimethylsilicone, trifluoropropylmethylsilicone, colloidal silica, a polyalkyl acrylate, a polyalkylmethacrylate, an alcohol ethoxy/propoxylate, a fatty acid ethoxy/propoxylate, and a sorbitan partial fatty acid ester. The defoamer may be incorporated normally at 10 to 100 mg/l.

Examples of the antioxidant according to the present teachings may include one or more of amine-based antioxidants, e.g., alkylated diphenylamine, phenyl-α-naphtylamine and alkylated phenyl-x-naphtylamine; phenol-based ones, e.g., 2,6-di-t-butyl phenol, 4,4'-methylenebis-(2,6-di-t-butyl phenol) and isooctyl-3-(3,5-di-t-butyl-4-hydroxyphenyl)propionate; and/or sulfur-based antioxidants, e.g., dilauryl-3,3'-thiodipropionate; and zinc dithiophosphate. The antioxidant may be incorporated normally at 0.05 wt. % to 5 wt. % of the total weight of the lubricating fluid.

Examples of the rust inhibitor according to the present teachings may include one or more of a fatty acid, alkenylsuccinic acid half ester, fatty acid soap, alkylsulfonate, polyhydric alcohol/fatty acid ester, fatty acid amine, oxidized paraffin, and alkylpolyoxyethylene ether. The rust inhibitor may be incorporated normally at 0 wt. % to 37 wt. % of the total weight of the lubricating fluid.

Examples of the friction modifier according to the present teachings may include one or more of an organomolybdenum-based compound, higher alcohols such as oleyl alcohol and stearyl alcohol; fatty acids such as oleic acid and stearic acid; esters such as oleyl glycerin ester, steryl glycerin ester, and lauryl glycerin ester; amides such as lauryl amide, oleyl amide, and stearyl amide; amines such as laurylamine, oleylamine, stearylamine, and an alkyldiethanolamine; and ethers such as lauryl glycerin ether and oleyl glycerin ether, oil/fat, amine, sulfided ester, phosphoric acid ester, acid phosphoric acid ester, acid phosphorous acid ester and amine salt of phosphoric acid ester. The friction modifier may be incorporated normally at 0.05 wt. %. to 5 wt. % of the total weight of the lubricating fluid.

Examples of the extreme pressure additive according to the present teachings may include one or more of organic sulfur, phosphorus or chlorine compounds, including sulfur-phosphorus and sulfur-phosphorus-boron compounds, which chemically react with the metal surface under high pressure conditions.

Examples of the anti-wear additive according to the present teachings may include one or more of zinc dithiophosphate, zinc dialkyl dithio phosphate, tricresyl phosphate, halocarbons (chlorinated paraffins), glycerol mono oleate, and stearic acid.

Examples of the corrosion inhibitor according to the present teachings may include zinc dithiophosphates.

Examples of the pour point depressant according to the present teachings may include one or more of ethylene/vinyl acetate copolymer, condensate of chlorinated paraffin and naphthalene, condensate of chlorinated paraffin and phenol, polymethacrylate, polyalkyl styrene, and so forth. The pour point depressant may be incorporated normally at 0.1 wt. % to 10 wt. % of the total weight of the lubricating fluid.

In addition, solubilizing agent (i.e., co-solvents) that are used to dissolve polar additives in usually less polar or unpolar base oils may be included according to the present teachings.

A total content of additive(s) in the lubricating fluid composition of the present teachings is not limited. However, one or more additives (including the above-described solubilizing agent) may be incorporated at 1 wt. % to 30 wt. % of the total weight of the lubricating fluid, preferably 2 wt. % to 15 wt. % of the total weight of the lubricating fluid.

Figure 2:
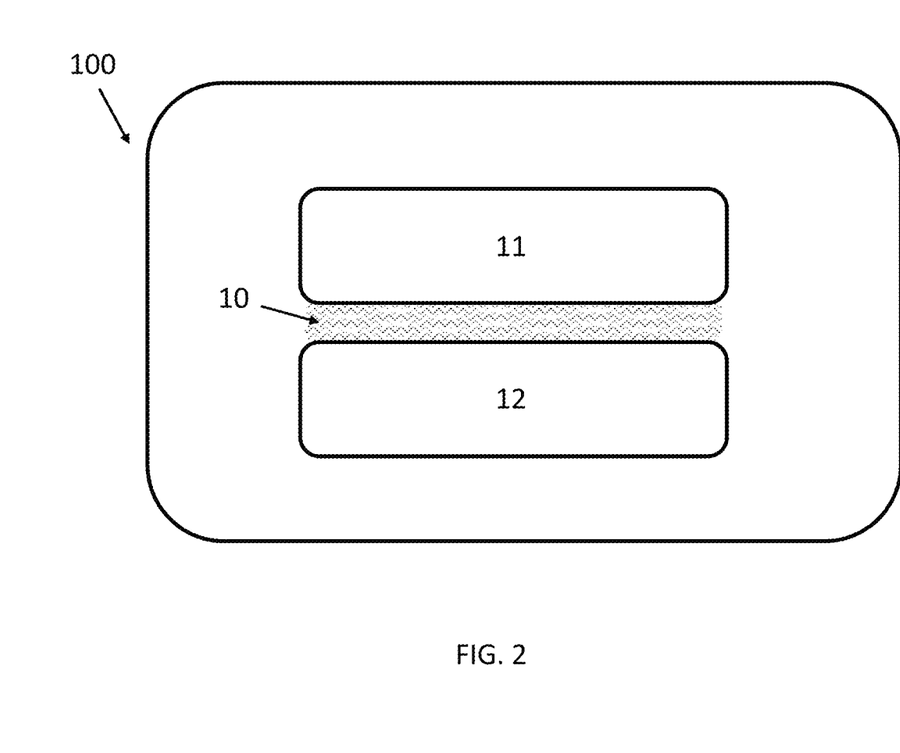
FIG. 2 illustrates a manner of using the lubricating fluid according to the present teachings.

Referring to FIG. 2, the lubricating fluid 10 according to the present teachings is applied and used between two mechanical parts 11, 12 of a machine 100, for example a motor or engine. The lubricating fluid 10 has improved low temperature performance, as well as minimized elastohydrodynamic shear strength, and enables the mechanical parts 11, 12 to operate in the elastohydrodynamic regime in lubrication. Thus, the present teachings provide a machine comprising two parts and the lubricating fluid applied between the two parts, and provide a process of using the lubricating fluid including applying the lubricating fluid between two parts included in a machine.

The lubricating fluid according to the present teachings may comprise at least one additive selected from a group consisting of: oxidation inhibitors, metallic dispersants, non-metallic dispersants, metallic detergents, non-metallic detergents, corrosion inhibitors, rust inhibitors, metal deactivators, metallic anti-wear agents, non-metallic anti-wear agents, phosphorus-containing anti-wear agents, non-phosphorus containing anti-wear agents, sulfur-containing anti-wear agents, non-sulfur containing anti-wear agents, metallic extreme pressure additives, non-metallic extreme pressure additives, phosphorus-containing extreme pressure additives, non-phosphorus containing extreme pressure additives, sulfur-containing extreme pressure additives, non-sulfur containing extreme pressure additives, anti-seizure agents, pour point depressants, wax modifiers, viscosity modifiers, seal compatibility agents, friction modifiers, lubricity agents, anti-staining agents, chromophoric agents, defoamants, demulsifiers, and a combination thereof.

The lubricating fluid according to the present teachings may further contain at least one of other lubricant base oils, and at least one of such base oil(s) is selected from a group consisting of mineral oil (i.e., Group I, II, II+, III, III+), polyalphaolefin (PAO) (Group IV), ester (Group V), polyalkylene glycol (PAG), ethylene-propylene oil, silicone oil and any other lubricating base oil used in lubricant and grease compounding.

The present teachings provide a lubricating fluid comprising a carboxyl di-ester of polyethylene glycol having the formula:

wherein $R_1$ and $R_2$ each independently comprise linear alkyl groups each having 5 to 11 carbon atoms, and wherein m ranges from 2 to 12. Each polyethylene oxide segment of the carboxyl di-ester of polyethylene glycol has an average molecular weight ranging from 200 g/mole to 400 g/mole. $R_1$ and $R_2$ are each independently derived from a mixture comprising octanoic carboxylic acid and decanoic carboxylic acid. $R_1$ and $R_2$ are each independently derived from hexanoic carboxylic acid. The lubricating fluid has a traction coefficient ranging from 0.001 μ to 0.015 μ when measured at a slide-to-roll ratio of 40 percent at a load of 20 N to 70 N at 90° C. The lubricating fluid has a 40° C. Kinematic Viscosity ranging from 13 cSt to 18 cSt. The lubricating fluid has a Viscosity Index ranging from 183 to 205. The lubricating fluid has a Freeze Point ranging from −25° C. to −38° C. The lubricating fluid further comprises at least one additive selected from the group consisting of: antioxidant, extreme pressure additive, anti-wear additive, friction modifier, rust inhibitor, corrosion inhibitor, detergent, dispersant, defoamer, and combinations thereof. The carboxyl di-ester of polyethylene glycol is a liquid at 25° C.

The present teachings also provide a lubricating fluid comprising: a carboxyl di-ester of polyethylene glycol having the formula:

and a carboxyl di-ester of polytetramethylene glycol having the formula:

wherein $R_1$ and $R_2$ each independently comprise linear alkyl groups each having 5 to 11 carbon atoms, and wherein m ranges from 2 to 12; and wherein $R_3$ and $R_4$ each independently comprise linear alkyl groups each having 5 to 11 carbon atoms, and wherein n ranges from 2 to 6. Each polyethylene oxide segment of the carboxyl di-ester of polyethylene glycol has an average molecular weight ranging from 200 g/mole to 400 g/mole, and each polytetramethylene oxide segment of the carboxyl di-ester of polytetramethylene glycol has an average molecular weight ranging from 200 g/mole to 400 g/mole. $R_1$, $R_2$, $R_3$, and $R_4$ are each independently derived from a mixture of octanoic carboxylic acid and decanoic carboxylic acid. $R_1$, $R_2$, $R_3$, and $R_4$ are each independently derived from hexanoic carboxylic acid. The lubricating fluid has a traction coefficient ranging from 0.001 μ to 0.015 μ when measured at a slide-to-roll ratio of 40 percent at a load of 20 N to 70 N at 90° C. The lubricating fluid has a 40° C. Kinematic Viscosity ranging from 13 cSt to 21 cSt. The lubricating fluid has a Viscosity Index ranging from 183 to 213. The lubricating fluid has a Freeze Point ranging from −7° C. to −38° C. The lubricating fluid further comprises at least one additive selected from the group consisting of: antioxidant, extreme pressure additive, anti-wear additive, friction modifier, rust inhibitor, corrosion inhibitor, detergent, dispersant, defoamer and combinations thereof. Each of the carboxyl di-ester of polyethylene glycol and the carboxyl di-ester of polytetramethylene glycol is a liquid at 25° C.

The present teachings further provide a method of manufacturing a lubricating fluid. The method comprises providing a polyethylene glycol; providing an acid; mixing the polyethylene glycol and the acid into a mixture for forming a carboxyl di-ester of polyethylene glycol; and filtering the mixture to form the carboxyl di-ester of polyethylene glycol for the lubricating fluid, wherein the carboxyl di-ester of polyethylene glycol has the structure:

wherein $R_1$ and $R_2$ each independently comprise linear alkyl groups each having 5 to 11 carbon atoms, and wherein m ranges from 2 to 12. The acid may comprise a combination of octanoic carboxylic acid and decanoic carboxylic acid. The acid may comprise hexanoic carboxylic acid. The method further comprises mixing the polyethylene glycol and the acid with a catalyst, an antioxidant, and an azeotropic agent. The catalyst comprises dibutyltin oxide, the antioxidant comprises sodium hypophosphite, and the azeotropic agent comprises xylenes. The method further comprises treating the mixture to reduce an acid number by using calcium carbonate, sodium carbonate, or any suitable alkali metal carbonate, propylene carbonate, or glycidyl neodecanoate. Treating and filtering are completed when the acid number is equal to or less than 0.4 mg KOH/g.

The present teachings further provide a method of manufacturing a lubricating fluid. The method comprises providing a polytetramethylene glycol; providing a polyethylene glycol; providing an acid; mixing the polytetramethylene glycol, the polyethylene glycol, and the acid into a mixture for forming a carboxyl di-ester of polyethylene glycol and a carboxyl di-ester of polytetramethylene glycol; and filtering the mixture to form the carboxyl di-ester of polyethylene glycol and the carboxyl di-ester of polytetramethylene glycol for the lubricating fluid, wherein the carboxyl di-ester of polyethylene glycol has the formula:

wherein the carboxyl di-ester of polytetramethylene glycol has the formula:

wherein $R_1$ and $R_2$ each independently comprise linear alkyl groups each having 5 to 11 carbon atoms, and wherein m ranges from 2 to 12; and wherein $R_3$ and $R_4$ each independently comprise linear alkyl groups each having 5 to 11 carbon atoms, and wherein n ranges from 2 to 6. The acid comprises a combination of octanoic carboxylic acid and decanoic carboxylic acid. The combination comprises normal C8 and C10 carboxylic acids at a weight ratio between 60/40 and 80/20. The acid comprises hexanoic carboxylic acid. The method further comprises mixing the polytetramethylene glycol, the polyethylene glycol, and the acid with an azeotropic agent. The azeotropic agent comprises xylenes. The mixing is completed when an acid number is equal to or less than 1 mg KOH/g. The method further comprises treating the mixture to reduce an acid number by using calcium carbonate or sodium carbonate. The treating is completed when the acid number is equal to or less than 0.1 mg KOH/g.

The present teachings further provide a method of manufacturing a lubricating fluid. The method comprises providing a polyethylene glycol; providing a diacid; providing an acid; mixing the polyethylene glycol and the diacid into a first mixture; mixing the first mixture with the acid into a second mixture for forming a complex carboxyl diester of polyethylene glycol; and filtering the second mixture to form the complex carboxyl diester of polyethylene glycol for the lubricating fluid, wherein the complex carboxyl diester of polyethylene glycol has the structure of:

wherein $R_6$ and $R_7$ each independently comprise linear alkyl groups each having 5 to 11 carbon atoms; wherein $R_5$ is a dicarboxylic acid, comprising linear alkyl groups having 24-36 carbon atoms; wherein o ranges from 2-12; and wherein p ranges from 2-12. The diacid comprises oleic dimer acid. The method further comprises mixing the polyethylene glycol and the diacid with a catalyst, an antioxidant, and an azeotroping agent. The catalyst is dibutyltin oxide, the antioxidant is sodium hypophosphite, and the azeotroping agent is xylene. Mixing of the polyethylene glycol and the diacid is complete when the acid number is equal to or less than 0.5 mg KOH/g. The acid comprises hexanoic carboxylic acid or comprises octanoic carboxylic acid and decanoic carboxylic acid. Mixing the first mixture with the acid is completed when the hydroxyl number is no more than 10 mg KOH/g. The method further comprises treating the second mixture by using calcium carbonate, sodium carbonate, or any suitable alkali metal carbonate, propylene carbonate, or glycidyl neodecanoate. Treating and filtering are completed when the acid number is equal to or less than 0.4 mg KOH/g.

The present teachings further provide a method of manufacturing a lubricating fluid. The method comprises providing a polyethylene glycol; providing a polytetramethylene glycol; providing a diacid; providing an acid; mixing the polyethylene glycol, the polytetramethylene glycol, and the diacid into a first mixture; mixing the first mixture with the acid into a second mixture for forming a complex carboxyl diester of polyethylene glycol and polytetramethylene glycol; and filtering the second mixture to form the complex carboxyl diester of polyethylene glycol and polytetramethylene glycol for the lubricating fluid, wherein the complex carboxyl diester of polyethylene glycol and polytetramethylene glycol has the structure of:

wherein $R_9$ and $R_{10}$ each independently comprise linear alkyl groups each having 5 to 11 carbon atoms; wherein $R_8$ is a dicarboxylic acid, comprising linear alkyl groups having 24-36 carbon atoms; wherein q ranges from 2-12 and wherein r ranges from 2-6. The diacid comprises oleic dimer acid. The method further comprises mixing the polyethylene glycol, the polytetramethylene glycol, and the diacid with a catalyst, an antioxidant, and an azeotroping agent. The catalyst is dibutyltin oxide, the antioxidant is sodium hypophosphite, and the azeotroping agent is xylene. Mixing of the polyethylene glycol, the polytetramethylene glycol, and the diacid is complete when the acid number is equal to or less than 0.5 mg KOH/g. The acid comprises hexanoic carboxylic acid or comprises octanoic carboxylic acid and decanoic carboxylic acid. Mixing the first mixture with the acid is completed when the hydroxyl number is equal to or less than 10 mg KOH/g. The method further comprises treating the second mixture by using calcium carbonate, sodium carbonate, or any suitable alkali metal carbonate, propylene carbonate, or glycidyl neodecanoate. Treating and filtering are completed when the acid number is equal to or less than 0.4 mg KOH/g.

While the present teachings have been described above in terms of specific embodiments, it is to be understood that they are not limited to those disclosed embodiments. Many modifications and other embodiments will come to mind to those skilled in the art to which this pertains, and which are intended to be and are covered by both this disclosure and the appended claims. For example, in some instances, one or more features disclosed in connection with one embodiment can be used alone or in combination with one or more features of one or more other embodiments. It is intended that the scope of the present teachings should be determined by proper interpretation and construction of any claims and their legal equivalents, as understood by those of skill in the art relying upon the disclosure in this specification and the attached drawings.

What is claimed is:

1. A lubricating fluid comprising:
a carboxyl di-ester of polyethylene glycol having the Formula:

a carboxyl di-ester of polytetramethylene glycol having the Formula:

wherein $R_1$ and $R_2$ are each independently derived from a mixture of octanoic carboxylic acid and decanoic carboxylic acid or derived from hexanoic carboxylic acid, and wherein m ranges from 2 to 12; and wherein $R_3$ and $R_4$ are each independently linear alkyl groups each having 5 to 11 carbon atoms, and wherein n ranges from 2 to 6.

2. The lubricating fluid of claim 1, wherein each polyethylene oxide segment of the carboxyl di-ester of polyethylene glycol has an average molecular weight ranging from 200 g/mole to 400 g/mole, and each polytetramethylene oxide segment of the carboxyl di-ester of polytetramethylene glycol has an average molecular weight ranging from 200 g/mole to 300 g/mole.

3. The lubricating fluid of claim 1, wherein $R_3$ and $R_4$ are each independently derived from a mixture of octanoic carboxylic acid and decanoic carboxylic acid or derived from hexanoic carboxylic acid.

4. The lubricating fluid of claim 1, wherein the lubricating fluid has a traction coefficient ranging from 0.026 μ to 0.008 μ when measured at a slide-to-roll ratio of 190 percent at 1.0 GPa maximum contact stress at 40° C. to 120° C. for 1 to 3 m/s entrainment velocity.

5. The lubricating fluid of claim 1, wherein the lubricating fluid has a 40° C. Kinematic Viscosity ranging from 13 cSt to 21 cSt.

6. The lubricating fluid of claim 1, wherein the lubricating fluid has a Viscosity Index ranging from 183 to 213.

7. The lubricating fluid of claim 1, wherein the lubricating fluid has a Freeze Point below −7° C.

8. The lubricating fluid of claim 1, further comprising at least one additive selected from the group consisting of: oxidation inhibitors, metallic dispersants, non-metallic dispersants, metallic detergents, non-metallic detergents, corrosion inhibitors, rust inhibitors, metal deactivators, metallic anti-wear agents, non-metallic anti-wear agents, phosphorus-containing anti-wear agents, non-phosphorus containing anti-wear agents, sulfur-containing anti-wear agents, non-sulfur containing anti-wear agents, metallic extreme pressure additives, non-metallic extreme pressure additives, phosphorus-containing extreme pressure additives, non-phosphorus containing extreme pressure additives, sulfur- containing extreme pressure additives, non-sulfur containing extreme pressure additives, anti-seizure agents, pour point depressants, wax modifiers, viscosity modifiers, seal compatibility agents, friction modifiers, lubricity agents, anti-staining agents, chromophoric agents, defoamants, demulsifiers, and a combination thereof.

9. The lubricating fluid of claim 1, further comprising at least one lubricant base oil selected from a group consisting of: mineral oil, polyalphaolefin, ester, polyalkylene glycol, ethylene-propylene oil, silicone oil, and a combination thereof.

10. A machine comprising two parts and the lubricating fluid of claim 1 applied between the two parts.

11. A process of using the lubricating fluid of claim 1 that comprises applying the lubricating fluid between two parts included in a machine.

12. A lubricating fluid comprising a carboxyl di-ester composition comprising a mixture of at least two different compounds selected from the group consisting of:
a carboxyl di-ester of polyethylene glycol having the Formula:

(1)

wherein $R_1$ and $R_2$ each independently comprise linear alkyl groups each having 5 to 11 carbon atoms, and wherein m ranges from 2 to 12;
a complex carboxyl di-ester of polyethylene glycol having the Formula:

(3)

wherein $R_6$ and $R_7$ each independently comprise linear alkyl groups each having 5 to 11 carbon atoms, wherein $R_5$ comprises linear alkyl group having 24 to 36 carbon atoms, wherein o ranges from 2 to 12, and wherein p ranges from 2 to 12; and
a complex carboxyl di-ester of polyethylene glycol and polytetramethylene glycol having the Formula:

(4)

wherein $R_9$ and $R_{10}$ each independently comprise linear alkyl groups each having 5 to 11 carbon atoms, wherein $R_8$ comprises linear alkyl group having 24 to 36 carbon atoms, wherein q ranges from 2 to 12, and wherein r ranges from 2 to 6;

wherein a process of using the lubricating fluid comprises applying the lubricating fluid between two parts included in a machine.

13. The lubricating fluid of claim 12, wherein each polyethylene oxide segment of formulas (1), (3), and (4) has an average molecular weight ranging from 200 to 400 g/mole and each polytetramethylene oxide segment of Formula (4) has an average molecular weight ranging from 200 to 300 g/mole.

14. The lubricating fluid of claim 12, wherein $R_1$ and $R_2$ are each independently derived from a mixture of octanoic carboxylic acid and decanoic carboxylic acid or derived from hexanoic carboxylic acid.

15. The lubricating fluid of claim 12, wherein $R_6$ and $R_7$ are each independently derived from a mixture of octanoic carboxylic acid and decanoic carboxylic acid or derived from hexanoic carboxylic acid.

16. The lubricating fluid of claim 12, wherein $R_9$ and $R_{10}$ are each independently derived from a mixture of octanoic carboxylic acid and decanoic carboxylic acid or derived from hexanoic carboxylic acid.

17. The lubricating fluid of claim 12, wherein Rs and Rs are each derived from a dicarboxylic acid having 24 to 36 carbon atoms.

18. The lubricating fluid of claim 12, wherein the lubricating fluid has a traction coefficient ranging from 0.026 μ to 0.008 μ when measured at a slide-to-roll ratio of 190 percent at 1.0 GPa maximum contact stress at 40° C. to 120° C. for 1 to 3 m/s entrainment velocity.

19. The lubricating fluid of claim 12, wherein the lubricating fluid has a Freeze Point below −7° C.

20. The lubricating fluid of claim 12, further comprising at least one additive selected from the group consisting of: oxidation inhibitors, metallic dispersants, non-metallic dispersants, metallic detergents, non-metallic detergents, corrosion inhibitors, rust inhibitors, metal deactivators, metallic anti-wear agents, non-metallic anti-wear agents, phosphorus-containing anti-wear agents, non-phosphorus containing anti-wear agents, sulfur-containing anti-wear agents, non-sulfur containing anti-wear agents, metallic extreme pressure additives, non-metallic extreme pressure additives, phosphorus-containing extreme pressure additives, non-phosphorus containing extreme pressure additives, sulfur-containing extreme pressure additives, non-sulfur containing extreme pressure additives, anti-seizure agents, pour point depressants, wax modifiers, viscosity modifiers, seal compatibility agents, friction modifiers, lubricity agents, anti-staining agents, chromophoric agents, defoamants, demulsifiers, and a combination thereof.

21. The lubricating fluid of claim 12, further comprising at least one lubricant base oil selected from a group consisting of: mineral oil, polyalphaolefin, ester, polyalkylene glycol, ethylene-propylene oil, silicone oil, and a combination thereof.

22. A machine comprising two parts and the lubricating fluid of claim 12 applied between the two parts.

23. A lubricating fluid comprising:
a carboxyl di-ester of polyethylene glycol having the Formula:

(1)

a carboxyl di-ester of polytetramethylene glycol having the Formula:

(2)

wherein $R_1$ and $R_2$ are each independently linear alkyl groups each having 5 to 11 carbon atoms, and wherein m ranges from 2 to 12; and wherein $R_3$ and $R_4$ are each independently derived from a mixture of octanoic carboxylic acid and decanoic carboxylic acid or derived from hexanoic carboxylic acid, and wherein n ranges from 2 to 6.

* * * * *

UNITED STATES PATENT AND TRADEMARK OFFICE
CERTIFICATE OF CORRECTION

PATENT NO. : 11,820,952 B2
APPLICATION NO. : 17/380768
DATED : November 21, 2023
INVENTOR(S) : Thomas Reginald Forbus, Jr.

Page 1 of 1

It is certified that error appears in the above-identified patent and that said Letters Patent is hereby corrected as shown below:

In the Claims

Column 23, Line 40, Claim 12, in Equation 3, delete the leftmost instance of "R5" and replace with -- R6 --

Column 24, Line 21, Claim 17, delete the leftmost instance of "Rs" and replace with -- R5 --

Column 24, Line 21, Claim 17, delete the rightmost instance of "Rs" and replace with -- R8 --

Signed and Sealed this
Twenty-fourth Day of June, 2025

Coke Morgan Stewart
*Acting Director of the United States Patent and Trademark Office*